US009820801B2

(12) United States Patent
Anderer

(10) Patent No.: US 9,820,801 B2
(45) Date of Patent: Nov. 21, 2017

(54) EPILATION BY THERMOLYSIS

(71) Applicant: Suzanne Anderer, Frankfort, IL (US)

(72) Inventor: Suzanne Anderer, Frankfort, IL (US)

( * ) Notice: Subject to any disclaimer, the term of this patent is extended or adjusted under 35 U.S.C. 154(b) by 349 days.

(21) Appl. No.: 14/728,187

(22) Filed: Jun. 2, 2015

(65) Prior Publication Data
US 2015/0342666 A1 Dec. 3, 2015

Related U.S. Application Data

(60) Provisional application No. 62/006,941, filed on Jun. 3, 2014.

(51) Int. Cl.
A61B 18/14 (2006.01)
A61B 18/12 (2006.01)
A61N 1/32 (2006.01)
A61B 18/00 (2006.01)

(52) U.S. Cl.
CPC ...... *A61B 18/1206* (2013.01); *A61B 18/1477* (2013.01); *A61B 2018/00017* (2013.01); *A61B 2018/00476* (2013.01); *A61B 2018/00732* (2013.01); *A61B 2018/00761* (2013.01); *A61B 2018/00767* (2013.01); *A61B 2018/1425* (2013.01); *A61N 1/32* (2013.01)

(58) Field of Classification Search
CPC .. A61N 1/32; A61B 18/1206; A61B 18/1477; A61B 2018/00017; A61B 2018/00476; A61B 2018/00732; A61B 2018/00761; A61B 2018/00767; A61B 2018/1425
See application file for complete search history.

(56) References Cited

U.S. PATENT DOCUMENTS

| 3,815,603 | A | * | 6/1974 | Sramek | A61B 18/14 606/36 |
| 4,174,714 | A | | 11/1979 | Mehl | |
| 4,216,775 | A | | 8/1980 | Cottingham | |
| 4,550,728 | A | * | 11/1985 | Runyon | A61B 18/14 128/908 |
| 4,598,709 | A | | 7/1986 | Smith | |
| 4,940,466 | A | | 7/1990 | Paduano | |
| 2004/0073079 | A1 | * | 4/2004 | Altshuler | A61B 5/6843 600/1 |
| 2009/0125015 | A1 | | 5/2009 | Smal | |
| 2010/0114091 | A1 | * | 5/2010 | Eckhouse | A45D 26/00 606/36 |
| 2011/0125151 | A1 | * | 5/2011 | Strauss | A61B 18/1206 606/37 |

* cited by examiner

*Primary Examiner* — Michael Peffley
(74) *Attorney, Agent, or Firm* — Global Intellectual Property Agency, LLC; Daniel Enea

(57) ABSTRACT

A method for removing hair by thermolysis is provided. The method steps include oscillating a direct current to create an alternating current ("AC") micro-pulse, pulsing the AC micro-pulse on and off continuously, delivering the AC micro-pulse to a probe, applying the probe to a hair follicle, and inverting the direction of the AC micro-pulse on the hair follicle. When the probe is applied to the hair follicle, the AC micro-pulse travels from the top of the dermis of the hair follicle to a dermal papilla of the hair follicle. The AC micro-pulse reverses direction at the dermal papilla and travels to the top of the dermis of the hair follicle. The AC micro-pulse produces heat that destroys the tissues controlling the growth of the hair follicle.

13 Claims, 3 Drawing Sheets

EPILATION BY THERMOLYSIS

CROSS REFERENCE TO RELATED APPLICATION

Figure 1:
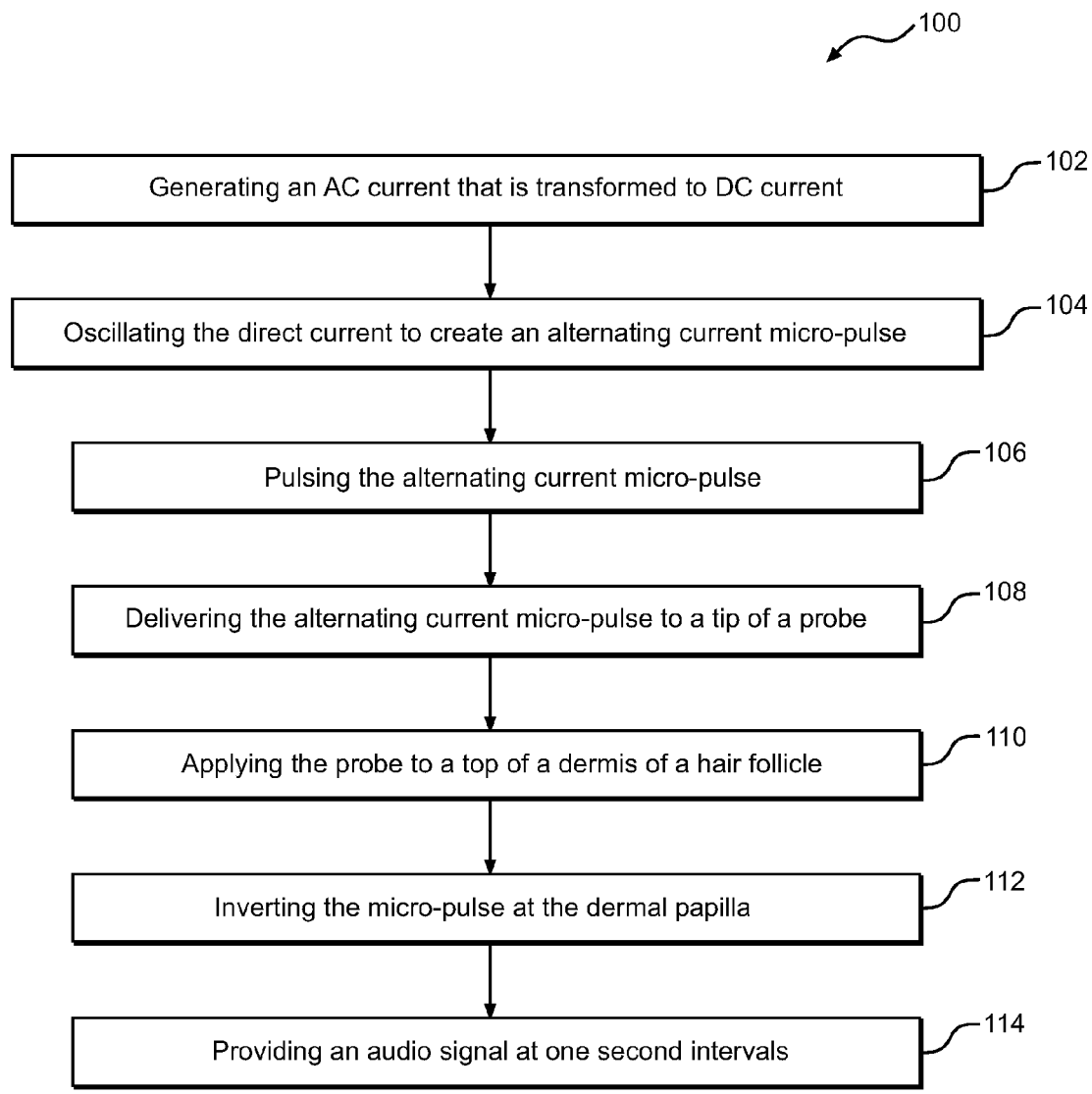

This application claims the benefit of U.S. Provisional Application No. 62/006,941 filed on Jun. 3, 2014. The above identified patent application is herein incorporated by reference in its entirety to provide continuity of disclosure.

FIELD OF THE INVENTION

The invention generally relates to a method for hair removal. More particularly, the present invention relates to a method of epilating hair using thermoylsis by sequentially applying an inverted AC micro-pulse to a hair follicle which produces heat that destroys the tissue controlling current and future growth of a hair follicle.

BACKGROUND OF THE INVENTION

Many people suffer from unwanted hair growth on their face and body. While some depilatories and laser hair removal treatments offer temporary relief, various other techniques have been developed in an effort to provide for permanent hair removal. In general, these techniques have proved to be either painful, or ineffective in producing permanent hair removal.

Techniques for permanent hair removal generally fall into one of three categories: electrolytic, thermolytic, or a blend of electrolytic and thermolytic techniques. Electrolytic epilation, as applied to a method of hair removal, refers to a technique in which a galvanic or direct current (DC) is directed to the papilla of a hair in order to initiate a chemical reaction in which water and salt in the cell tissue surrounding the hair follicle are electrolyzed, so that sodium hydroxide is formed. The sodium hydroxide, being caustic, destroys the papilla, resulting in permanent hair removal.

Thermolytic epilation refers to a method of permanent hair removal in which a high frequency, or radio frequency (RF), current is applied to the hair or hair follicle. The RF current generates heat, which destroys the hair follicle.

Several devices illustrate variations on one or more of these methods. U.S. Pat. No. 4,155,363 issued to Letchworth et al., describes a machine which provides a constant direct current to a plurality of filament (wire needle) electrodes, regardless of the electrical load. The machine is also capable of providing pulsed direct current, or of reversing the polarity of the direct current. U.S. Pat. No. 4,598,709, issued to Smith et al., discloses a machine which is capable of delivering either a direct current only, a high frequency RF current only, or a blend of galvanic and RF current through a wire needle probe. U.S. Pat. No. 4,821,717, issued to J. M. M. Wehrli, teaches a barbed needle which can be used with either the electrolytic, thermolytic, or blend methods.

The foregoing patents have described devices which use an invasive technique for permanent hair removal, i.e., they all involve the insertion of a needle through the skin closely adjacent the hair follicle. Several patents describe devices directed towards non-invasive techniques for hair removal. U.S. Pat. No. 2,888,927 to E. M. Fozard, describes a method of hair removal which uses an RF current directed through a pair of tweezers which are used to grasp the hair to be removed. U.S. Pat. No. 4,498,474 to Chalmers et al., teaches an epilation method which involves applying one, or preferably two, wetting fluids to the skin surrounding the hair, the wetting solutions having an ionic activity equivalent to at least 25 ppm sodium chloride in water, followed by applying an RF current to the hair through tweezers.

U.S. Pat. No. 5,026,369 to H. L. Cole, discloses an electrolytic method of hair removal which involves applying a saline type electrode solution comprising 85% glycerin, 14% water, 0.5% salt, and 0.5% copper sulphate to the hair, and then applying a direct or galvanic current to the hair through tweezers. A series of patents issued to T. L. Mehr, Sr., and to Mehr et al., including U.S. Pat. No. 5,470,332, U.S. Pat. No. 5,868,738, and U.S. Pat. No. 6,063,076, teach techniques for removing multiple hairs simultaneously using either electrolytic, thermolytic, or blend techniques. The '332 patent teaches application of a multiple layer material, including a nonconductive adhesive layer against the skin, a conductive adhesive layer above the first layer, and a structural layer above the conductive layer. The '738 patent adds disclosure concerning wetting the hair with a liquid solution and using a comb to remove, multiple hairs. The '076 patent describes a conductive layer which also includes a cold wax material.

None of the above inventions and patents, taken either singly or in combination, is seen to describe the instant invention as claimed. Thus a method of hair removal solving the aforementioned problems is desired.

SUMMARY OF THE INVENTION

In view of the foregoing disadvantages inherent in the known types of hair removal methods now present in the prior art, the present invention provides a method for epilating hair by thermolysis wherein the same can be utilized for providing convenience for the user when permanently removing hair and preventing regrowth of hair.

It is therefore an object of the present invention to provide a new and improved method for hair removal that has all of the advantages of the prior art and none of the disadvantages.

It is another an object of the present invention to provide a method for epilating hair using a thermolytic process. The method includes generating an AC current. The AC current is delivered at 13.56 megahertz (mHz) and remains constant throughout the application of the AC current. In alternate embodiments, the AC current can be delivered at 27.12 and 40.68 mHz.

It is another an object of the present invention to provide a method for epilating hair including oscillating the AC current to create an AC micro-pulse, wherein the AC micro-pulse is standardized at a constant frequency.

It is another an object of the present invention to provide a method for epilating hair including pulsing the AC micro-pulse. The AC micro-pulse is pulsed via continuously switching the AC micro-pulse on and off at a predetermined pulse rate The AC current may pulsed at a rate of 90-200 pulses per second. The pulsing may be done periodically via an electrolysis unit.

It is another an object of the present invention to provide a method for epilating hair including delivering the AC micro-pulse to a probe. The hair follicle aligns with the probe, regardless of follicle shape, due to the point effect of the probe. The AC micro-pulse changes from a negative charge to a positive charge at the tip of the probe.

It is another object of the present invention to provide a method for epilating hair including applying the probe to a top of a dermis of a hair follicle. The AC micro-pulse travels from the top of the dermis of the hair follicle to a dermal papilla of the hair follicle.

It is another an object of the present invention to provide a method for epilating hair including inverting the AC micro-pulse. The AC micro-pulse reverses direction at the dermal papilla and travels to the top of the dermis of the hair follicle.

It is another an object of the present invention to provide a method for epilating hair including providing an audio signal at one second intervals. The audio signal communicates the seconds elapsed which relates to the depth the AC micro-pulse travels down the hair follicle.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 1 shows a flowchart of the method for removing hair by thermolysis according to one embodiment of the present invention.

Figure 2:
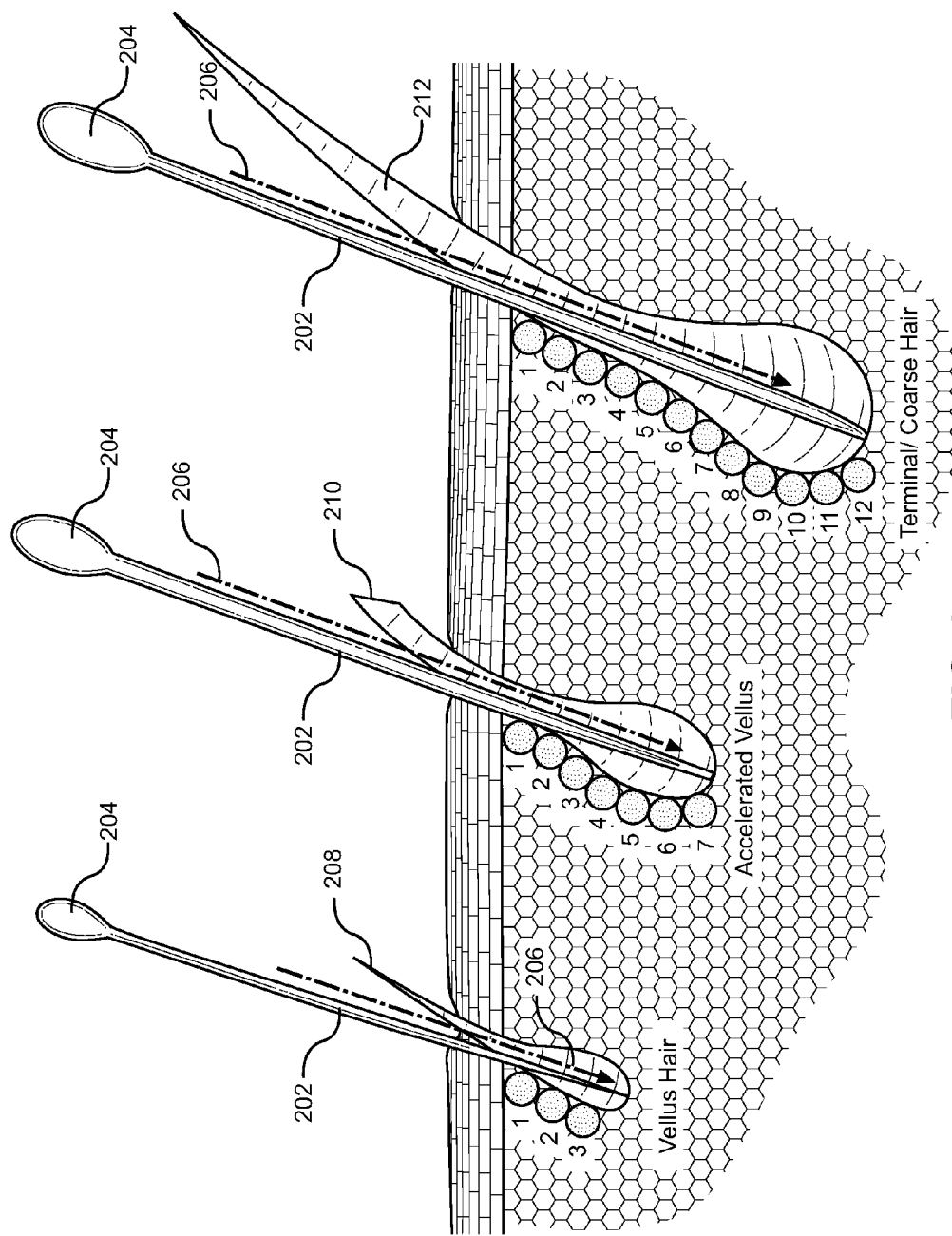
Figure 3A:
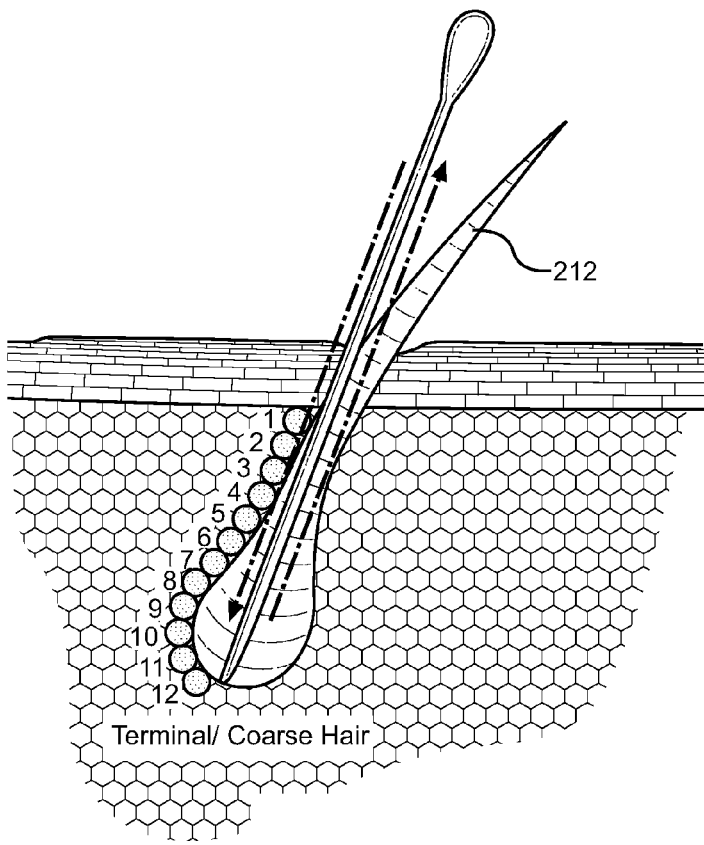
Figure 3B:
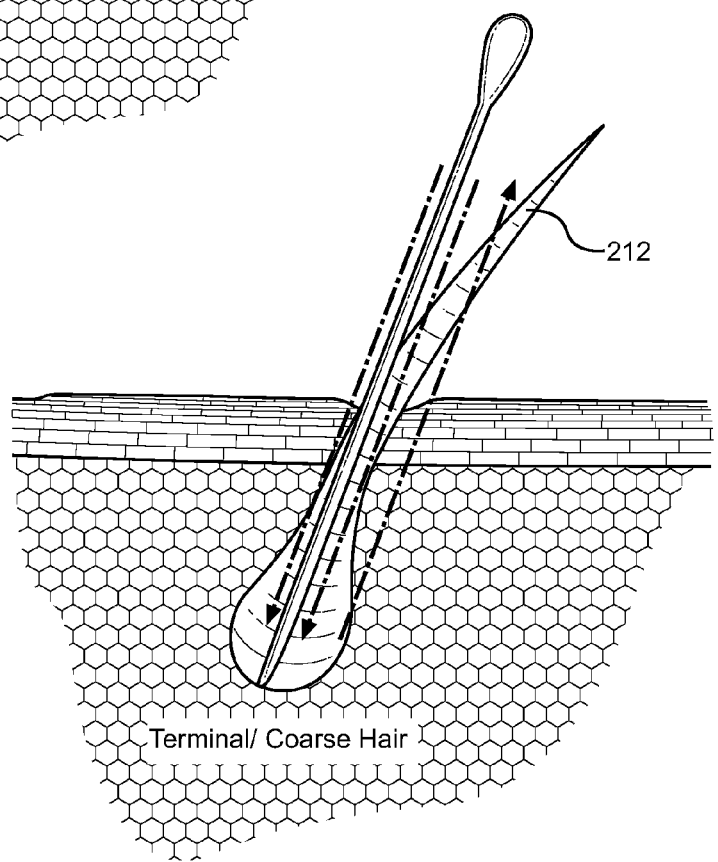

FIGS. 2 and 3A-B, show a filament insertion of the probe into the hair follicle in a plurality of modes according to multiple embodiments of the present invention.

DETAILED DESCRIPTION OF THE INVENTION

Reference is made herein to the attached drawings. Like reference numerals are used throughout the drawings to depict like or similar elements of the method for removing hair by electrolysis. For the purposes of presenting a brief and clear description of the present invention, the preferred embodiment will be discussed as used for removing hair. The figures are intended for representative purposes only and should not be considered to be limiting in any respect.

Referring now to FIG. 1, there is shown a flowchart of the method for removing hair by thermolysis according to one embodiment of the present invention. The method 100 begins with the generating step 102. At the generating step 102, an alternating current ("AC") is generated via an electrolysis unit. The AC current is delivered at 60 cycles per second to the electrolysis unit, which is the standard AC current cycle delivered to households in the United States. The AC current is then changed into direct current via transformers, capacitors, and filters. After the generating step 102, the method continues to the oscillating step 104.

At oscillating step 104, the direct current enters an oscillator to create an AC micro-pulse required for thermolysis. The AC micro-pulse is standardized at a constant frequency by the oscillator. In a preferred embodiment, the AC micro-pulse is standardized at 13.56 megahertz (MHz). Other radio frequencies used during the thermolysis process are 27.12 MHz and 40.68 MHz. After the oscillating step 104, the method continues to pulsing step 106.

At pulsing step 106, the AC mirco-pulse is pulsed via continually switching on and off the AC micro-pulse at a predetermined pulse rate. The AC micro-pulse is standardized at 13.56 MHz before the micro-pulse is conditioned by the pulsing. The intensity of the micro-pulse is controlled by the voltage supplied, approximately 30 to 95, but the micro-pulse always remains at a frequency of 13.56 MHz. The AC current is pulsed by being continually turned on and off at a rate of 90-200 pulses per second. In a preferred embodiment, the current is pulsed at a rate of 200 pulses per second rather than 100 pulses per second because it is a more comfortable pulse rate for treatment. The AC micro-pulse operates continuously as long as the current is actively engaged.

The automatic and continuous switching on and off of the 13.56 MHz AC micro-pulse maximizes treatment efficacy while at the same time minimizing unwanted tissue damage. This process reduces the discomfort experienced from the intensity levels of the micro-pulsed current necessary to accomplish permanent hair removal. After pulsing step 106, the method continues to the delivering step 108.

At the delivering step 108, the AC micro-pulse is delivered to a tip of a probe. The AC micro-pulses that emanate from the tip of the probe, leads the probe into the follicle at the top of the dermis of the hair follicle. The AC micro-pulsing current is activated all the way to the deepest, anagen-depth level of the hair follicle.

The electrical purpose of the 13.56 MHz micro-pulse current is to produce a radio wave current, oscillating at 13.56 million times per second that changes from a positive to a negative charge at the tip of the probe. This causes the ions in the salt water molecules of moist, sterile human tissue surrounding the hair in the follicle to move back and forth at that same frequency (13.56 MHz), producing heat through the friction of the rapid micro-pulsing or vibration.

The biological purpose of the 13.56 MHz micro-pulse, or radio frequency (RF), is to produce heat that destroys the tissues controlling the current and future growth of the hair being treated. Visible hair growth is largely controlled by the nourishment found in the blood circulating in the matrix of the pilosebaceous unit and the dermal papilla of the pilosebaceous unit. The AC micro-pulse heats and destroys the pilosebaceous unit. After the delivering step 108, the method continues to application step 110.

At the application step 110, the probe is applied to a visible hair at the top of the dermis of the visible hair follicle. The AC micro-pulse travels from the top of the dermis of the hair follicle to a dermal papilla. The probe delivering the AC micro-pulse starts the application at the top of the dermis and moves downward at a rate of approximately 1 mm per half second. The AC micro-pulse continues to the depth of the dermal papilla (deepest, anagen level), and if necessary, is inverted. In an alternate embodiment, the probe further includes an air flow that flows around the circumference of the tip of the probe. The air flow serves as a nerve distractor and adds comfort when the probe is applied. The air flows around the circumference of the tip of the probe at room temperature to provide pain management while receiving treatment. After the application step 108, the method continues to the inversion step 110.

At the inversion step 110, the AC micro-pulse inverts direction and travels back up the hair shaft. The AC micro-pulse reverses direction at the dermal papilla and travels to the top of the dermis of hair follicle. The inversion process can be repeated one or more times, continuously moving at the same rate of approximately 1 mm per half second back to the top of the dermis of the hair follicle. The force of the micro-pulsing alternating current at the tip of the probe leads the heat energy from the top of the dermis to the deepest, anagen levels of the hair. This treats the entire follicle and all surrounding stem cells that have the potential to grow hair in the future.

In an alternate embodiment, the method 100 may further include a providing step 112. At the providing step, an auditory signal is provided every one second to indicate the depth of the AC mirco-pulse. The audio indicator correlates the duration of the hair treatment and the length of time in which micro-pulse current is engaged. A signal sounds every second the probe is applied so that a practitioner knows exactly how much time the current has been engaged within the follicle. The audio signal also assists the practitioner in making uniform movements while gauging the speed at which insertions are being made. Having auditory rather than visual signals is essential to gauge the speed of the insertion and determine treatment duration, while simultaneously allowing the practitioner to focus on the hair follicle being treated micro-surgically.

An electrolysis unit provides the micro-pulsing alternating current according to one embodiment of the present invention. The electrolysis unit comprises a housing that includes electrical components and a probe that are adapted to supply alternating current or direct current to a hair follicle. The electrolysis unit provides the micro-pulsing AC current to a tip of a probe which is applied to a hair follicle to destroy hair.

The electrolysis unit applies a formula that employs current times pulses per millimeter to equal treatment strength and duration (expressed in pulses per millimeter):

$$\text{Current } (c) \times \text{Time } (t) \text{ in seconds} = \text{Pulses } (p) \text{ per mm.} \quad (i)$$

The probe of the electrolysis unit is inserted into a hair follicle with the assistance of the heat energy produced from the AC micro-pulses. The micro pulses are very fast amounts of oscillating current ranging in frequency from 3 to 30 megahertz (3 million to 30 million cycles per second). The probe glides from the top of the dermis to the deepest, anagen levels following alongside the hair—composed of the cuticle, cortex and medulla. The probe most often does not intersect with any part of the hair. The AC micro-pulse destroys the hair permanently by using RF current in fluid, not just the medulla, and thereby destroys all stem cells that have the potential for future hair growth in that single pilosebaceous unit. This accomplished with only a single treatment for permanent hair removal.

Referring now to FIGS. 2 and 3A-B, there are shown a filament insertion of the probe into the hair follicle according to multiple embodiments of the present invention. The duration of the AC micro-pulse treatment on the hair follicle is determined primarily by the type of hair follicle being treated. The location, length, and width of a hair follicle are all factors in determining the duration of probe insertion in a hair follicle and the direction of the current. The filament of the probe aligns with hair follicle resulting from the heat energy of the AC micro-pulses. The probe glides from the top of the dermis to the deepest, anagen levels following alongside the hair. Depending on the length of the hair, probe is applied for different amount of time according to the above formula.

The electrolysis unit provides a plurality of modes for treating different types of hair follicles. In a first mode, the filament 202 of the probe 204 provides an AC micro-pulse that travels in a downward direction 206 from the tip of the hair follicle to the deepest, anagen level. In this mode, a vellus hair 208 having a length of 1.5 to 2.0 mm, is treated for 1-3 seconds and an accelerated vellus hair 210, having a length of 2.0-3.0 mm, is treated for 4-7 seconds. A terminal/coarse hair follicle 212 having a length of 3.0-3.5 mm is treated for 8-12 seconds. The electrolysis unit may be activated be via a foot pedal or automatic start mode. The foot pedal can be actuated on and off so that an administrator can manage the micro-pulses throughout the treatment.

The electrolysis unit further includes a millimeter gauge on the face of the unit. The millimeter gauge serves as a superimposition of the hair follicle on a scale gauge which compares the treated, extracted hair placed on the gauge to determine the correct depth of insertion of the probe for other hair of the same structure and/or type. In this way, an administrator can record data for future clinical evaluations for each treatment.

In alternate modes, the terminal/coarse hair follicle 212 may be treated with an AC micro-pulse that travels in a downward direction from the top of the dermis of the hair follicle to the dermal papilla followed by an upward current that reverses direction at the dermal papilla and travels upward from the bottom of the hair follicle. The reversed upward traveling current is a second treatment of the terminal/coarse hair follicle 212 and is applied for another 8-12 seconds. Subsequently, a third treatment may be applied to the terminal/coarse hair follicle 212. The third treatment is downward moving current applied for yet another 8-12 seconds. In an alternate mode, the terminal/coarse hair follicle 212 is treated for 8-12 seconds with a downward moving current followed by a treatment for 8-12 seconds of an upward moving current.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method for removing hair by thermolysis, comprising:
   oscillating a direct current to create an alternating current micro-pulse, wherein the alternating current micro-pulse is standardized at a constant frequency;
   pulsing the alternating current micro-pulse, wherein the alternating current micro-pulse is pulsed via continuously switching the alternating current micro-pulse on and off at a predetermined pulse rate;
   delivering the alternating current micro-pulse to a tip of a probe, wherein the alternating current micro-pulse changes from a negative charge to a positive charge at the tip of the probe;
   applying the probe to a top of a dermis of a hair follicle, wherein the alternating current micro-pulse travels from the top of the dermis of the hair follicle to a dermal papilla of the hair follicle; and
   inverting the micro-pulse at the dermal papilla, wherein the alternating current micro-pulse reverses direction at the dermal papilla and travels to the top of the dermis of the hair follicle.

2. The method of claim 1, wherein the alternating current micro-pulse enters an oscillator to create the micro-pulse at 13.56 megahertz.

3. The method of claim 1, wherein the intensity of the alternating current micro-pulse is controlled via adjusting a voltage in the range of 30 to 95 volts.

4. The method of claim 1, wherein the alternating current micro-pulse is continuously turned on and off at a rate of 100 pulses per second.

5. The method of claim 1, wherein the alternating current micro-pulse is continuously turned on and off at a rate of 200 pulses per second.

6. The method of claim 1, wherein the alternating current micro-pulse is generated via a foot pedal connected to an electrolysis unit.

7. The method of claim 1, further comprising providing an audio signal at one second intervals.

8. The method of claim 1, wherein the probe comprises a sterile stainless steel applicator, wherein a top portion of the probe includes a needle pin.

9. The method of claim 1, wherein the probe further includes an air flow at room temperature that surrounds a circumference of the probe.

10. A method for removing hair by thermolysis, comprising:

generating an alternating current at 13.56 megahertz (MHz);

providing a voltage in the range of 30 to 95 volts to control the intensity of the alternating current, wherein the alternating current is maintained at 13.56 megahertz;

pulsing the alternating current to create an alternating current micro-pulse, wherein the alternating current micro-pulse is pulsed via continuously switching the alternating current micro-pulse on and off at a rate of 200 pulses per second;

delivering the alternating current micro-pulse to a probe;

producing heat via rapidly pulsing the alternating current micro-pulse;

applying the probe to a top of a dermis of a hair follicle, wherein the alternating current micro-pulse travels from the top of the dermis of the hair follicle to a dermal papilla of the hair follicle; and providing an audio signal at one second intervals.

11. The method of claim 10, wherein the alternating current is continuously turned on and off at a rate of 100 pulses per second.

12. The method of claim 10, wherein the alternating current is generated via a foot pedal connected to an electrolysis unit.

13. The method of claim 10, further comprising inverting the alternating current micro-pulse at the dermal papilla, wherein the alternating current micro-pulse reverses direction at the dermal papilla and travels to the top of the dermis of the hair follicle.

* * * * *